(12) United States Patent
Shinozaki (10) Patent No.: US 9,757,838 B2
(45) Date of Patent: Sep. 12, 2017

(54) POLISHING APPARATUS HAVING END POINT DETECTING APPARATUS DETECTING POLISHING END POINT ON BASIS OF CURRENT AND SLIDING FRICTION

(71) Applicant: Ebara Corporation, Tokyo (JP)

(72) Inventor: Hiroyuki Shinozaki, Tokyo (JP)

(73) Assignee: Ebara Corporation, Tokyo (JP)

( * ) Notice: Subject to any disclaimer, the term of this patent is extended or adjusted under 35 U.S.C. 154(b) by 48 days.

(21) Appl. No.: 14/727,234

(22) Filed: Jun. 1, 2015

(65) Prior Publication Data

US 2015/0343594 A1 Dec. 3, 2015

(30) Foreign Application Priority Data

Jun. 3, 2014 (JP) ................................. 2014-114672

(51) Int. Cl.
| | |
|---|---|
| *B24B 49/10* | (2006.01) |
| *B24B 49/16* | (2006.01) |
| *B24B 37/013* | (2012.01) |
| *B24B 37/10* | (2012.01) |
| *G01N 19/02* | (2006.01) |

(52) U.S. Cl.
CPC .......... *B24B 37/013* (2013.01); *B24B 37/107* (2013.01); *B24B 49/10* (2013.01); *B24B 49/16* (2013.01); *G01N 19/02* (2013.01)

(58) Field of Classification Search
CPC ... B24B 37/013; B24B 37/046; B24B 37/107; B24B 49/10; B24B 49/16; G01N 19/02

USPC .......................................................... 384/448
See application file for complete search history.

(56) References Cited

U.S. PATENT DOCUMENTS

| | | | | |
|---|---|---|---|---|
| 3,115,034 A * | 12/1963 | De Hart | ................ | G01L 3/1485 73/54.39 |
| 5,036,015 A * | 7/1991 | Sandhu | ................. | B24B 37/013 216/84 |
| 5,597,341 A * | 1/1997 | Kodera | ................. | B24B 37/013 257/E21.244 |
| 6,213,846 B1 * | 4/2001 | Li | ........................ | B24B 37/013 451/2 |
| 6,257,953 B1 * | 7/2001 | Gitis | ..................... | B24B 37/013 451/287 |

(Continued)

FOREIGN PATENT DOCUMENTS

JP H10-202523 A 8/1998

*Primary Examiner* — Joseph J Hail
*Assistant Examiner* — Arman Milanian
(74) *Attorney, Agent, or Firm* — Leydig, Voit & Mayer, Ltd.

(57) ABSTRACT

A polishing apparatus includes: a polishing table 12 for holding a polishing pad; a first electric motor 14 that rotationally drives the polishing table 12; a first rotary joint 40 that has a rotating body 41 that is rotationally driven by the first electric motor 14, a housing 42 provided around the rotating body 41, and a seal portion 44 that seals between the rotating body 41 and the housing 42; a second current sensor 31 that detects a current which is correlated with driving load of the first electric motor 14; a friction detecting unit 50 that detects sliding friction in the seal portion 44 of the first rotary joint 40; and an end point detecting apparatus 60 that detects a polishing end point of the polishing target on the basis of the current and the sliding friction.

22 Claims, 6 Drawing Sheets

(56) References Cited

U.S. PATENT DOCUMENTS

| | | | | |
|---|---|---|---|---|
| 6,709,314 | B2* | 3/2004 | Kaushal | B24B 49/10 |
| | | | | 451/10 |
| 2001/0006870 | A1* | 7/2001 | Moore | B24B 49/006 |
| | | | | 451/5 |
| 2002/0037681 | A1* | 3/2002 | Gitis | B24B 37/013 |
| | | | | 451/5 |
| 2002/0052166 | A1* | 5/2002 | Kojima | B24B 37/013 |
| | | | | 451/5 |
| 2002/0090889 | A1* | 7/2002 | Crevasse | B24B 37/013 |
| | | | | 451/8 |
| 2002/0106971 | A1* | 8/2002 | Rodriquez | B24B 53/017 |
| | | | | 451/5 |
| 2002/0173223 | A1* | 11/2002 | Gitis | B24B 37/013 |
| | | | | 451/5 |
| 2003/0109194 | A1* | 6/2003 | Wang | B24B 37/013 |
| | | | | 451/5 |
| 2005/0061674 | A1* | 3/2005 | Wang | B23H 5/06 |
| | | | | 205/78 |
| 2005/0136800 | A1* | 6/2005 | Miller | B24B 37/013 |
| | | | | 451/5 |
| 2007/0087662 | A1* | 4/2007 | Benvegnu | B24B 37/013 |
| | | | | 451/5 |
| 2008/0071414 | A1* | 3/2008 | Fujita | B24B 37/013 |
| | | | | 700/121 |
| 2008/0287043 | A1* | 11/2008 | Saito | B24B 49/14 |
| | | | | 451/285 |
| 2010/0311309 | A1* | 12/2010 | Shinozaki | B24B 49/08 |
| | | | | 451/5 |
| 2013/0122788 | A1* | 5/2013 | Chang | B24B 37/013 |
| | | | | 451/59 |

* cited by examiner

POLISHING APPARATUS HAVING END POINT DETECTING APPARATUS DETECTING POLISHING END POINT ON BASIS OF CURRENT AND SLIDING FRICTION

CROSS REFERENCE TO RELATED APPLICATION

This application claims priority to Japanese Patent Application No. 2014-114672 filed Jun. 3, 2014, the entire contents of which are hereby incorporated by reference.

The present invention relates to a polishing apparatus.

BACKGROUND OF THE INVENTION

In recent years, following the high integration of semiconductor devices, wirings of circuits have been miniaturized, and the distance between the wirings has also been reduced. Therefore, it is necessary to flatten the surface of a semiconductor wafer, which is a polishing target, and as one of the flattening methods, a semiconductor wafer is polished by using a polishing apparatus.

Conventionally, the polishing apparatus includes a polishing table for holding a polishing pad for polishing the polishing target, and a top ring holding the polishing target to be pressed onto the polishing pad. The polishing table and the top ring are rotationally driven by driving units (for example, motors), respectively. While a liquid (slurry) containing abrasive powder is poured onto the polishing pad, the polishing target held on the top ring is pressed thereonto, so that the polishing target is polished.

In the polishing apparatus, if the polishing target is insufficiently polished, there arises a concern that circuits are not insulated from each other, which causes short circuit with each other. Moreover, in the case of excessive polishing, the cross-sectional area of the wiring decreases to cause such problems that the resistance value increases, or the wiring itself is completely removed and thereby the circuit itself is not formed. Due to this, the polishing apparatus is required to perform optimum detection of the polishing end point.

As a polishing end point detection method, there is known a method of detecting a change in polishing friction force at the time when a different material begins to be polished with progress of the polishing (Japanese Patent Laid-Open No. 10-202523). A semiconductor wafer which is a polishing target has a layered structure formed of different materials including a semiconductor, a conductor and an insulator. The different material layers have different coefficients of friction therebetween. Therefore, in this method, the change in polishing friction force arising from a different material layer beginning to be polished is detected. According to the method, the time when the polishing reaches the different material layer is the end point of the polishing.

Moreover, the polishing apparatus can detect the polishing end point by detecting a change in polishing friction force at the time when the polishing surface of the polishing target changes from being not flat to being flat.

Herein, the polishing friction force arising in polishing the polishing target can be seen as driving load of the driving unit. For example, in the case where the driving unit is an electric motor, the driving load (torque) can be measured as a current flowing through the motor. Due to this, the motor current is detected by a current sensor, and thereby, the end point of polishing can be detected on the basis of the detected change in motor current.

The conventional technology, however, does not consider improvement of accuracy of the polishing end point detection.

Namely, the polishing apparatus is sometimes provided with a rotary joint for the purpose of supplying cooling water or the like to the polishing table or the top ring. The rotary joint includes a rotating body which is rotationally driven by a driving unit which drives the polishing table or the top ring, a housing provided around the rotating body, a bearing which is provided between the rotating body and the housing to support rotation of the rotating body, a seal portion which seals between the rotating body and the housing, and the like. The seal portion includes a mechanical seal, an oil seal and the like between the rotating body and the housing. In the seal portion, sliding friction due to the rotating body and the housing arises, and the sliding friction results in driving load of the driving unit which drives the rotating body.

Accordingly, the motor current detected by the current sensor contains not only the driving load due to the polishing friction force but also the driving load due to the sliding friction of the seal portion in the rotary joint. When some cause results in a change in driving load due to the sliding friction of the seal portion, there is a concern that this change is directly reflected to the motor current and causes false detection of the polishing end point.

Therefore, an object of an aspect of the present invention is to improve accuracy of polishing end point detection.

SUMMARY OF INVENTION

In view of the above-mentioned problem to be solved, there is provided a polishing apparatus according to an aspect of the present invention, including: a polishing table for holding a polishing pad for polishing a polishing target; a first driving unit that rotationally drives the polishing table; a first rotary joint that has a rotating body that is rotationally driven by the first driving unit, a housing provided around the rotating body, and a seal portion that seals between the rotating body and the housing; a current detecting unit that detects a current which is correlated with driving load of the first driving unit; a friction detecting unit that detects sliding friction in the seal portion of the first rotary joint; and an end point detecting apparatus that detects a polishing end point of the polishing target on the basis of the current detected by the current detecting unit and the sliding friction detected by the friction detecting unit.

Moreover, in view of the above-mentioned problem to be solved, there is provided a polishing apparatus according to an aspect of the present invention, including: a substrate holding unit that holds a polishing target to be pressed onto a polishing pad for polishing the polishing target; a second driving unit that rotationally drives the holding unit; a second rotary joint that has a rotating body that is rotationally driven by the second driving unit, a housing provided around the rotating body, and a seal portion that seals between the rotating body and the housing; a current detecting unit that detects a current which is correlated with driving load of the second driving unit; a friction detecting unit that detects sliding friction in the seal portion of the second rotary joint; and an end point detecting apparatus that detects a polishing end point of the polishing target on the basis of the current detected by the current detecting unit and the sliding friction detected by the friction detecting unit.

Moreover, the polishing apparatus according to an aspect further includes: a first rotation stopping member fixed to the housing; and a second rotation stopping member that comes into contact with the first rotation stopping member to stop rotation of the housing, wherein the friction detecting unit can include a force detecting unit that detects contact force between the first rotation stopping member and the second rotation stopping member.

Moreover, in an aspect of the polishing apparatus, the force detecting unit can include at least one of a load cell, a strain gauge, a pressure sensor and a piezoelectric element provided on at least one of contact portions between the first rotation stopping member and the second rotation stopping member.

Moreover, the polishing apparatus according to an aspect further includes: a first rotation stopping member fixed to the housing, and a second rotation stopping member that comes into contact with the first rotation stopping member to stop rotation of the housing, wherein the friction detecting unit can include a motion detecting unit that detects a physical quantity caused by a displacement of the first rotation stopping member.

Moreover, in an aspect of the polishing apparatus, the motion detecting unit can include at least one of a displacement sensor, a speed sensor and an acceleration sensor provided on the first rotation stopping member.

Moreover, in an aspect of the polishing apparatus, on at least one of contact portions between the first rotation stopping member and the second rotation stopping member, an elastic member which undergoes elastic deformation in accordance with contact therebetween may be provided.

Moreover, in an aspect of the polishing apparatus, the end point detecting apparatus can include a signal processing unit that generates a signal for detection of a polishing end point of the polishing target on the basis of the current detected by the current detecting unit and the sliding friction detected by the friction detecting unit, and an end point detecting unit that detects the polishing end point of the polishing target on the basis of the signal for detection of the polishing end point which is generated by the signal processing unit.

Moreover, in an aspect of the polishing apparatus, the signal processing unit can stop output of the signal for detection of the polishing end point when it is detected that a change larger than a threshold is contained in the sliding friction detected by the friction detecting unit.

Moreover, in an aspect of the polishing apparatus, the signal processing unit can configure a difference between a first signal which is correlated with the current detected by the current detecting unit and a second signal which is correlated with the sliding friction detected by the friction detecting unit as the signal for detection of the polishing end point.

Moreover, in an aspect of the polishing apparatus, the signal processing unit can include a band elimination filter that removes a predetermined frequency component from a second signal which is correlated with the sliding friction detected by the friction detecting unit, and can output the signal for detection of the polishing end point on the basis of the second signal from which the predetermined frequency component is removed by the band elimination filter and a first signal which is correlated with the current detected by the current detecting unit.

Moreover, in an aspect of the polishing apparatus, the signal processing unit can include an abnormality detection function in which a signal indicating that abnormality arises in the first or second rotary joint is outputted when it is detected that a change larger than a threshold is contained in the sliding friction detected by the friction detecting unit.

According to the present invention, accuracy of polishing end point detection can be improved.

DESCRIPTION OF EMBODIMENTS

Hereafter, a polishing apparatus according to an embodiment of the present invention is described based on the drawings. First, a basic configuration of the polishing apparatus is described, and after that, detection of the polishing end point of a polishing target is described.

Basic Configuration

Figure 1:
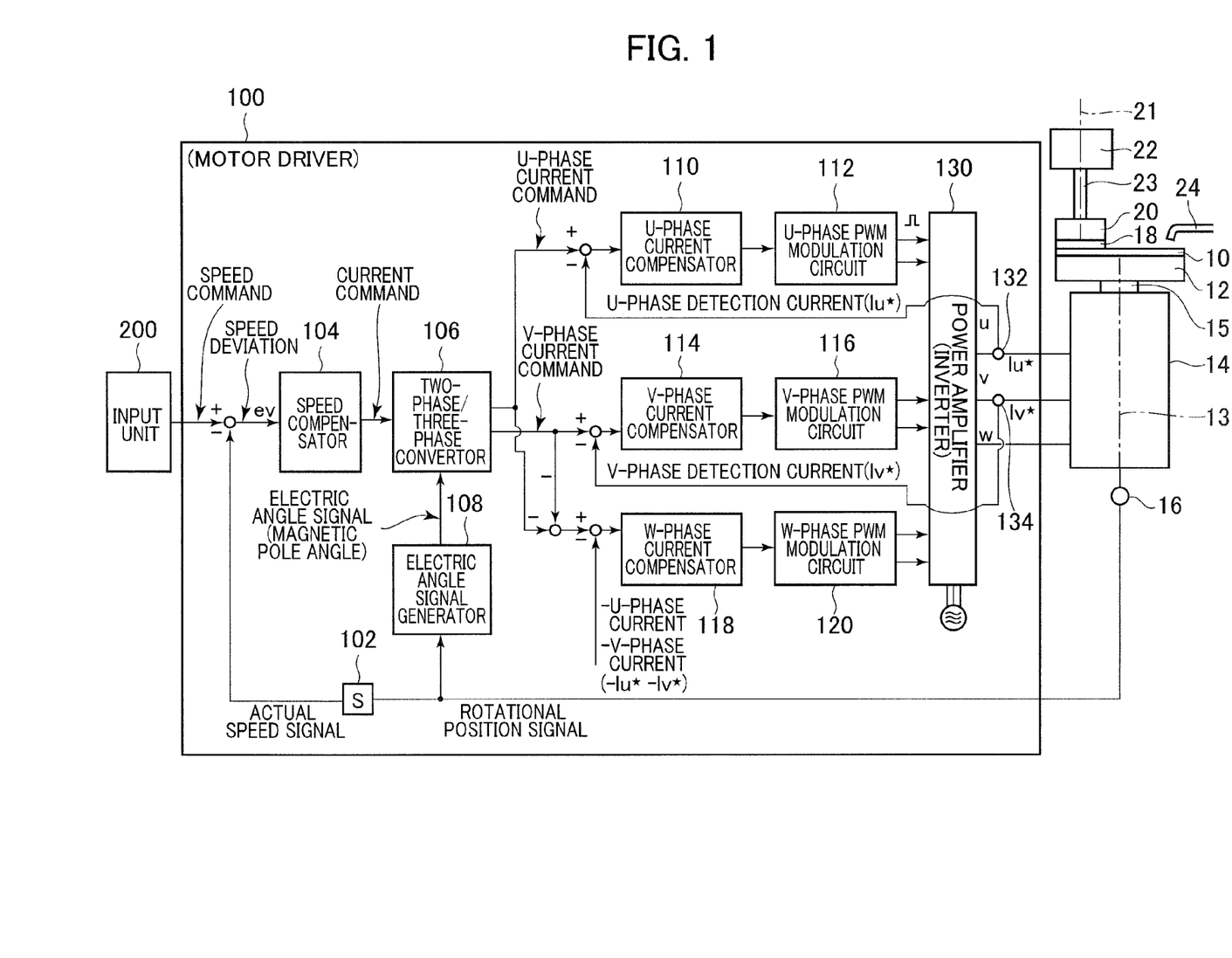
FIG. 1 is a diagram illustrating a basic configuration of a polishing apparatus according to an embodiment.

FIG. 1 is a diagram illustrating a basic configuration of a polishing apparatus according to the present embodiment. The polishing apparatus includes a polishing table 12 on the upper surface of which a polishing pad 10 can be attached, a first electric motor (first driving unit) 14 which rotationally drives the polishing table 12, a position detecting sensor 16 which detects the rotational position of the first electric motor, a top ring (substrate holding unit) 20 which can hold a semiconductor wafer 18, and a second electric motor (second driving unit) 22 which rotationally drives the top ring 20.

The top ring 20 can be brought close to and separated from the polishing table 12 by a not-shown holding apparatus. When the semiconductor wafer 18 is polished, the top ring 20 is brought close to the polishing table 12, and thereby, the semiconductor wafer 18 held by the top ring 20 is brought into contact with the polishing pad 10 attached to the polishing table 12.

When the semiconductor wafer 18 is polished, the semiconductor wafer 18 is pressed onto the polishing pad 10 by the top ring 20 holding the semiconductor wafer 18 in the state where the polishing table 12 is rotationally driven by the first electric motor 14. Moreover, the top ring 20 is rotationally driven by the second electric motor 22 about an axial line 21 which is deviated from a rotation axis 13 of the polishing table 12. When the semiconductor wafer 18 is polished, an abrasive liquid containing an abrasive material is supplied onto the upper surface of the polishing pad 10 from the abrasive material supply apparatus 24. The semiconductor wafer 18 set at the top ring 20 is pressed onto the polishing pad 10 on which the abrasive liquid is supplied in the state where the top ring 20 is rotationally driven by the second electric motor 22.

It is preferred that the first electric motor 14 is a synchronous-type or induction-type AC servomotor at least including three phase windings of a U-phase, a V-phase and a W-phase. In the present embodiment, the first electric motor 14 contains an AC servomotor including the three phase windings. The three phase windings are configured such that currents having phases shifted by 120 degrees from one another are allowed to flow through field windings provided around a rotor in the first electric motor 14, and thereby, the rotor is rotationally driven. The rotor of the first electric motor 14 is connected to a motor shaft 15 and the polishing table 12 is rotationally driven by the motor shaft 15.

It is preferred that the second electric motor 22 is a synchronous-type or induction-type AC servomotor at least including three phase windings of the U-phase, the V-phase and the W-phase. In the present embodiment, the second electric motor 22 contains an AC servomotor including the three phase windings. The three phase windings are configured such that currents having phases shifted by 120 degrees from one another are allowed to flow through field windings provided around a rotor in the second electric motor 22, and thereby, the rotor is rotationally driven. The rotor of the second electric motor 22 is connected to a motor shaft 23 and the top ring 20 is rotationally driven by the motor shaft 23.

Figure 4:
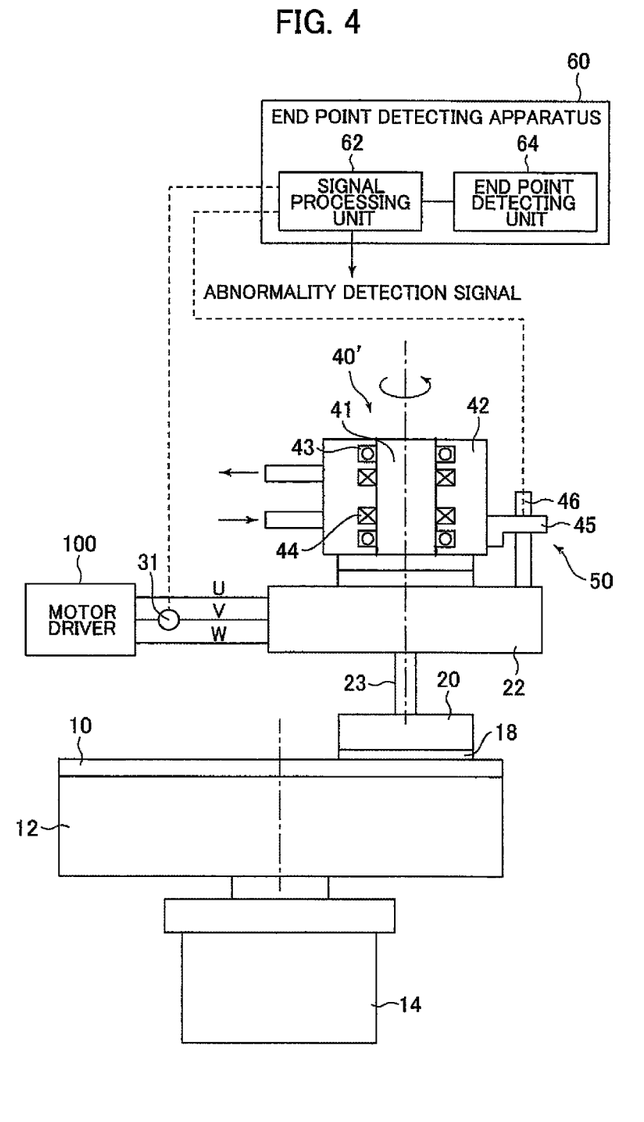
FIG. 4 is a diagram schematically illustrating a configuration of a polishing apparatus according to s second embodiment, regarding polishing end point detection.

Moreover, the polishing apparatus includes a motor driver 100 which rotationally drives the first electric motor 14, and an input unit 200 which accepts a command signal of the rotation speed of the first electric motor 14 from the operator via an input interface such as a keyboard and a touch panel. The input unit 200 inputs the accepted command signal to the motor driver 100. Notably, while in FIG. 1 the motor driver 100 that rotationally drives the first electric motor 14 is described, another motor driver 100 is similarly connected also to the second electric motor 22 as illustrated in FIG. 4.

The motor driver 100 includes a differentiator 102, a speed compensator 104, a two-phase/three-phase convertor 106, an electric angle signal generator 108, a U-phase current compensator 110, a U-phase PWM modulation circuit 112, a V-phase current compensator 114, a V-phase PWM modulation circuit 116, a W-phase current compensator 118, a W-phase PWM modulation circuit 120, a power amplifier 130 and current sensors 132 and 134.

The differentiator 102 differentiates a rotational position signal detected by the position detecting sensor 16, and thereby, generates an actual speed signal corresponding to an actual rotation speed of the first electric motor 14. Namely, the differentiator 102 is a calculator which obtains a rotation speed of the first electric motor 14 on the basis of a detection value of the rotational position of the first electric motor 14.

The speed compensator 104 compensates the rotation speed of the first electric motor 14 on the basis of a speed deviation signal corresponding to a deviation between the command signal (target value) of the rotation speed inputted via the input unit 200 and the actual speed signal generated by the differentiator 102. Namely, the speed compensator 104 generates a command signal of current to be supplied to the first electric motor 14 on the basis of a deviation between the command value of the rotation speed of the first electric motor 14 inputted via the input interface (input unit 200) and the rotation speed of the first electric motor 14 obtained by the differentiator 102.

The speed compensator 104 can be configured, for example, of a PID controller. In this case, the speed compensator 104 performs proportional control, integral control and differential control to generate the current command signal corresponding to the compensated rotation speed. In the proportional control, the operation amount is changed to be proportional to the deviation between the command signal of the rotation speed inputted from the input unit 200 and the actual speed signal of the first electric motor. In the integral control, the operation amount is changed to be proportional to the value of accumulation of the deviations. In the differential control, the operation amount is outputted to be proportional to the change rate of the deviation (in other words, the speed of change in deviation) being obtained. Notably, the speed compensator 104 may be configured of a PI controller.

The electric angle signal generator 108 generates an electric angle signal on the basis of the rotational position signal detected by the position detecting sensor 16. The two-phase/three-phase convertor 106 generates a U-phase current command signal and a V-phase current command signal on the basis of the current command signal generated by the speed compensator 104 and the electric angle signal generated by the electric angle signal generator 108. Namely, the two-phase/three-phase convertor 106 is a convertor which generates the current command values of at least two phases out of the phases on the basis of the electric angle signal generated on the basis of the detection value of the rotational position of the first electric motor 14 and the command signal of current generated by the speed compensator 104.

Figure 2:
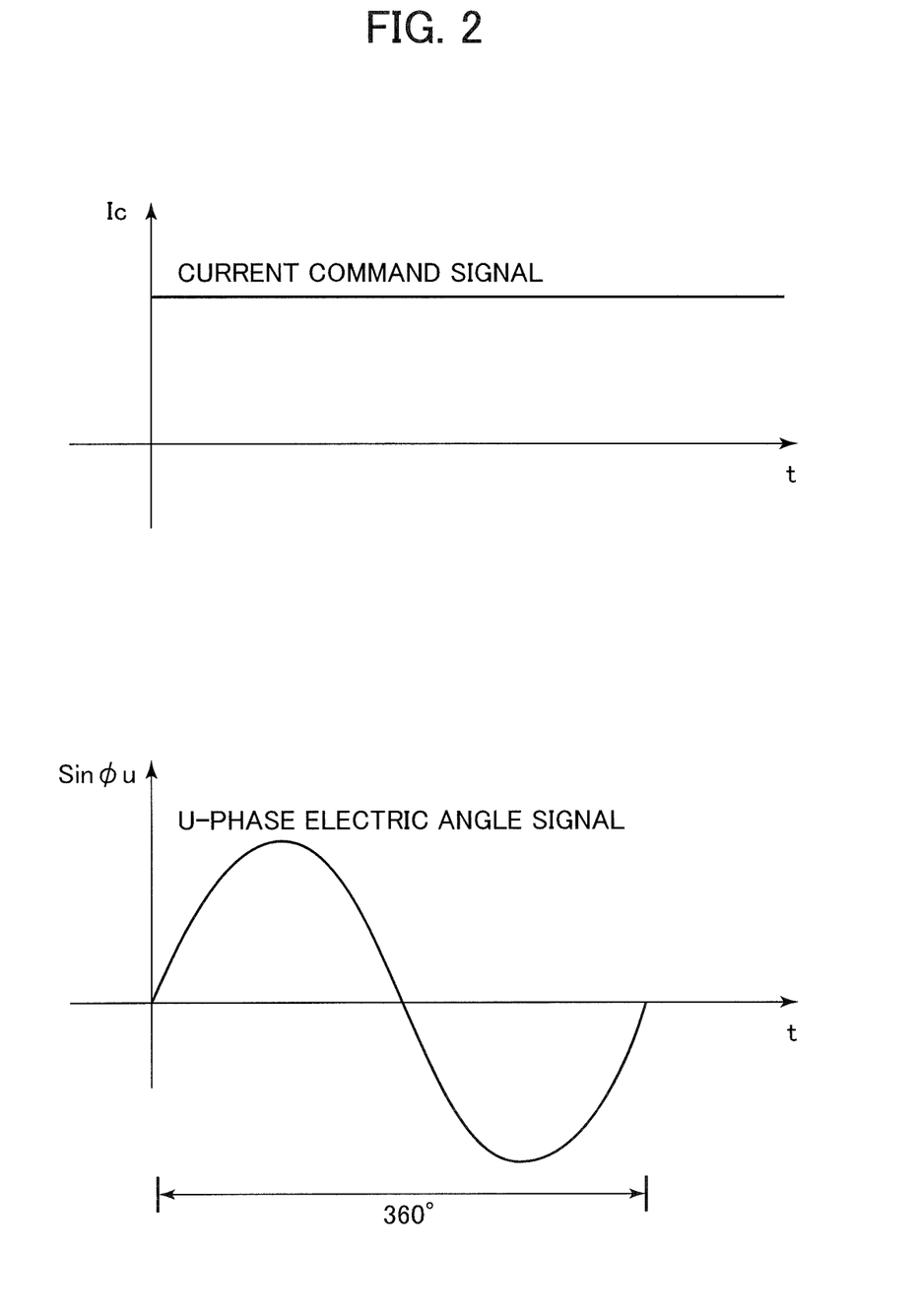
FIG. 2 is a diagram for explaining processing contents of a two-phase/three-phase convertor.

Herein, processing of the two-phase/three-phase convertor 106 is described in detail. FIG. 2 is a diagram for explaining processing contents of the two-phase/three-phase convertor. To the two-phase/three-phase convertor 106, a current command signal Ic as illustrated in FIG. 2 is inputted from the speed compensator 104. Moreover, to the two-phase/three-phase convertor 106, an electric angle signal Sinϕu of the U-phase as illustrated in FIG. 2 is inputted from the electric angle signal generator 108. Notably, while the illustration is omitted from FIG. 2, an electric angle signal Sinϕv of the V-phase is also inputted to the two-phase/three-phase convertor 106.

For example, the generation of the U-phase current command signal Iuc is considered. In this case, the two-phase/three-phase convertor 106 multiplies the current command signal Ic(i) by the electric angle signal Sinϕu(i) of the U-phase at time ti, and thereby, generates the U-phase current command signal Iuc(i). Namely, Iuc(i)=Ic(i)×Sinϕu(i). Moreover, similarly to the case of the U-phase, the two-phase/three-phase convertor 106 multiplies the current command signal Ic(i) by the electric angle signal Sinϕv(i) of the V-phase at time ti, and thereby, generates the V-phase current command signal Ivc(i). Namely, Ivc(i)=Ic(i)×Sinϕv(i).

The current sensor 132 is provided on a U-phase output line of the power amplifier 130 and detects the current of the U-phase outputted from the power amplifier 130. The U-phase current compensator 110 performs current compensation of the U-phase on the basis of a U-phase current deviation signal corresponding to a deviation between the U-phase current command signal Iuc outputted from the two-phase/three-phase convertor 106 and a U-phase detection current Iu* which is detected and fed back by the current sensor 132. The U-phase current compensator 110 can be configured, for example, of a PI controller or a PID controller. The U-phase current compensator 110 compensates the U-phase current using PI control or PID control to generate a U-phase current signal corresponding to the compensated current.

The U-phase PWM modulation circuit 112 performs pulse width modulation on the basis of the U-phase current signal generated by the U-phase current compensator 110. The U-phase PWM modulation circuit 112 performs the pulse width modulation, and thereby, generates pulse signals of two systems corresponding to the U-phase current signal.

The current sensor 134 is provided on a V-phase output line of the power amplifier 130 and detects the current of the V-phase outputted from the power amplifier 130. The V-phase current compensator 114 performs current compensation of the V-phase on the basis of a V-phase current deviation signal corresponding to a deviation between the V-phase current command signal Ivc outputted from the two-phase/three-phase convertor 106 and a V-phase detection current Iv* which is detected and fed back by the current sensor 134. The V-phase current compensator 114 can be configured, for example, of a PI controller or a PID controller. The V-phase current compensator 114 compensates the V-phase current using PI control or PID control to generate a V-phase current signal corresponding to the compensated current.

The V-phase PWM modulation circuit 116 performs pulse width modulation on the basis of the V-phase current signal generated by the V-phase current compensator 114. The V-phase PWM modulation circuit 114 performs the pulse width modulation, and thereby, generates pulse signals of two systems corresponding to the V-phase current signal.

The W-phase current compensator 118 performs current compensation of the W-phase on the basis of a W-phase current deviation signal corresponding to a deviation between a W-phase current command signal Iwc generated on the basis of the U-phase current command signal Iuc and the V-phase current command signal Ivc which are outputted from the two-phase/three-phase convertor 106, and the U-phase detection current Iu* and the V-phase detection current Iv* which are detected and fed back by the current sensors 132 and 134. The W-phase current compensator 118 can be configured, for example, of a PI controller or a PID controller. The W-phase current compensator 118 compensates the W-phase current using PI control and PID control to generate a W-phase current signal corresponding to the compensated current.

The W-phase PWM modulation circuit 120 performs pulse width modulation on the basis of the W-phase current signal generated by the W-phase current compensator 118. The W-phase PWM modulation circuit 118 performs the pulse width modulation, and thereby, generates pulse signals of two systems corresponding to the W-phase current signal.

To the power amplifier 130, the pulse signals of two systems which are generated by the U-phase PWM modulation circuit 112, the V-phase PWM modulation circuit 116 and the W-phase PWM modulation circuit 120 are applied. The power amplifier 130 drives individual transistors of an inverter unit provided inside the power amplifier 130 in response to the respective applied pulse signals. By doing so, the power amplifier 130 outputs AC power for each of the U-phase, the V-phase and the W-phase, and using this three-phase AC power, rotationally drives the first electric motor 14.

End Point Detection

Figure 3:
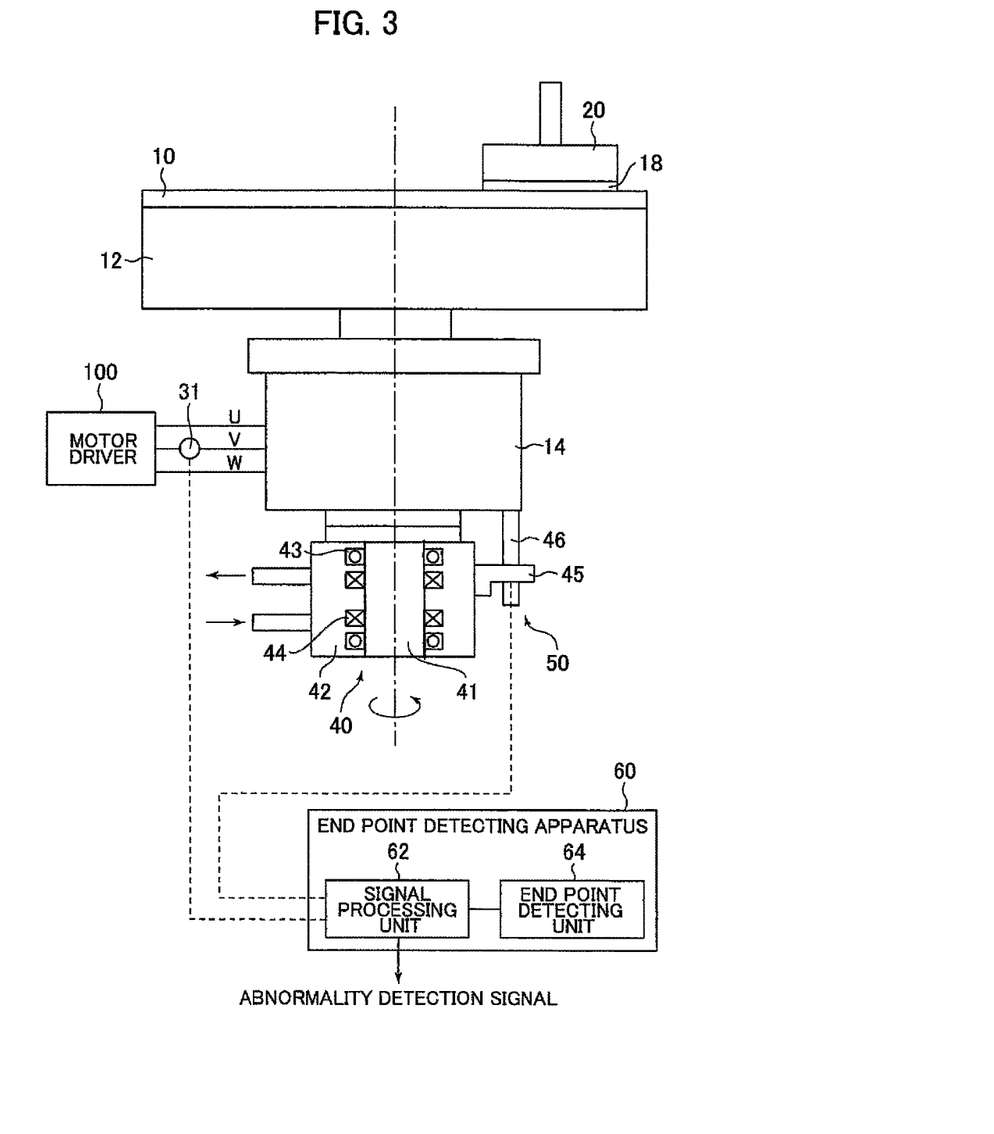
FIG. 3 is a diagram schematically illustrating a configuration of a polishing apparatus according to a first embodiment, regarding polishing end point detection.

Next, detection of the polishing end point of the polishing target is described. FIG. 3 is a diagram schematically illustrating a configuration of a polishing apparatus according to a first embodiment, regarding the polishing end point detection. FIG. 4 is a diagram schematically illustrating a configuration of a polishing apparatus according to a second embodiment, regarding the polishing end point detection. As illustrated in FIG. 3 and FIG. 4, the polishing apparatuses include a first rotary joint 40 on the first electric motor 14 side which rotationally drives the polishing table 12, and a second rotary joint 40' on the second electric motor 22 side which rotationally drives the top ring 20, respectively. Namely, the present invention can be applied to any of the first rotary joint 40 and the second rotary joint 40'. Notably, the first rotary joint 40 and the second rotary joint 40' have the similar configuration. Therefore, the components of the first rotary joint 40 and the second rotary joint 40' are collectively described using the same signs in the first embodiment and the second embodiment.

As illustrated in any of FIG. 3 and FIG. 4, a second current sensor (current detecting unit) 31 is provided for any one phase of the U-phase, the V-phase and the W-phase (V-phase in the first and second embodiments). The second current sensor 31 is provided on a current path of the V-phase between the motor driver 100 and the first electric motor 14 or on a current path of the V-phase between the motor driver 100 and the second electric motor 22. The second current sensor 31 detects the current of the V-phase to be outputted to an end point detecting apparatus 60.

Moreover, as illustrated in FIG. 3, the polishing apparatus according to the first embodiment includes the first rotary joint 40 for supplying cooling water onto the polishing table 12. As illustrated in FIG. 4, the polishing apparatus according to the second embodiment includes the second rotary joint 40' for supplying cooling water onto the top ring 20. Any of the first and second rotary joints 40 and 40' includes a rotating body 41 which is rotationally driven by the first electric motor 14 or the second electric motor 22, a housing 42 provided around the rotating body 41, bearings 43 which are provided between the rotating body 41 and the housing 42 and support the rotation of the rotating body 41, and seal portions 44 which seal between the rotating body 41 and the housing 42.

The seal portion 44 contains a mechanical seal in contact sliding between the rotating body 41 and the housing 42 and an oil seal. Contact surface force of the mechanical seal can be considered as difference force due to forces of the inside/outside fluids which act on the mechanical seal, spring force due to a spring, force preventing motion due to collapsing counterforce of an O-ring between a floating seal portion of the mechanical seal and a fixed wall, and the similar force. Sliding friction arises in relation between the contact surface force arising due to these and the state of the sliding interface (for example, the coefficient of friction). Moreover, this is affected by the influence of the relative speed, which is known as the Stribeck curve. Change in any of these causes change in sliding friction forces of the first and second rotary joints 40 and 40'. Moreover, any of these is converted into force in the rotation direction due to the state of the sliding interface. This state is known to be defined by the surface roughness and the wetting state of the contact surface.

Moreover, the polishing apparatus includes a first rotation stopping member 45 fixed to the housing 42 and a second rotation stopping member 46 which comes into contact with the first rotation stopping member 45 to stop the rotation of the housing 42, for each of the first and second rotary joints 40 and 40'. The first rotation stopping member 45 is a stay formed into a rod shape protruding outward from the outer surface of the housing 42. The second rotation stopping member 46 is a stay formed into a rod shape protruding downward from the lower surface of the first electric motor 14 or a stay formed into a rod shape protruding upward from the upper surface of the second electric motor 22. Drive of the first electric motor 14 or the second electric motor 22 rotates the rotating body 41. Rotation force of the rotating body 41 is delivered to the housing 42 via the seal portion 44, but the housing 42 stands still by its rotation prevented by the contact of the first rotation stopping member 45 with the second rotation stopping member 46. By doing so, the seal portion 44 in brought in contact sliding between the rotating body 41 and the housing 42. The sliding friction of the seal portion 44 is driving load of the first electric motor 14 or the second electric motor 22 driving the rotating body 41.

Accordingly, the motor current detected by the second current sensor 31 contains not only driving load due to polishing friction force arising in polishing the semiconductor wafer 18 but also the driving load due to the sliding friction of the seal portion 44 in the first or second rotary joint 40, 40'. There could be a concern of false detection of the polishing end point when some cause would result in change in driving load due to the sliding friction of the seal portion 44, this change being directly reflected on the motor current.

Therefore, the polishing apparatus includes a friction detecting unit 50 which detects the sliding friction in the seal portion 44 of the first or second rotary joint 40, 40'. Moreover, the polishing apparatus includes the end point detecting apparatus 60 which detects the polishing end point of the semiconductor wafer 18 on the basis of the current detected by the second current sensor 31 and the sliding friction detected by the friction detecting unit 50.

Friction Detecting Unit

Figure 5:
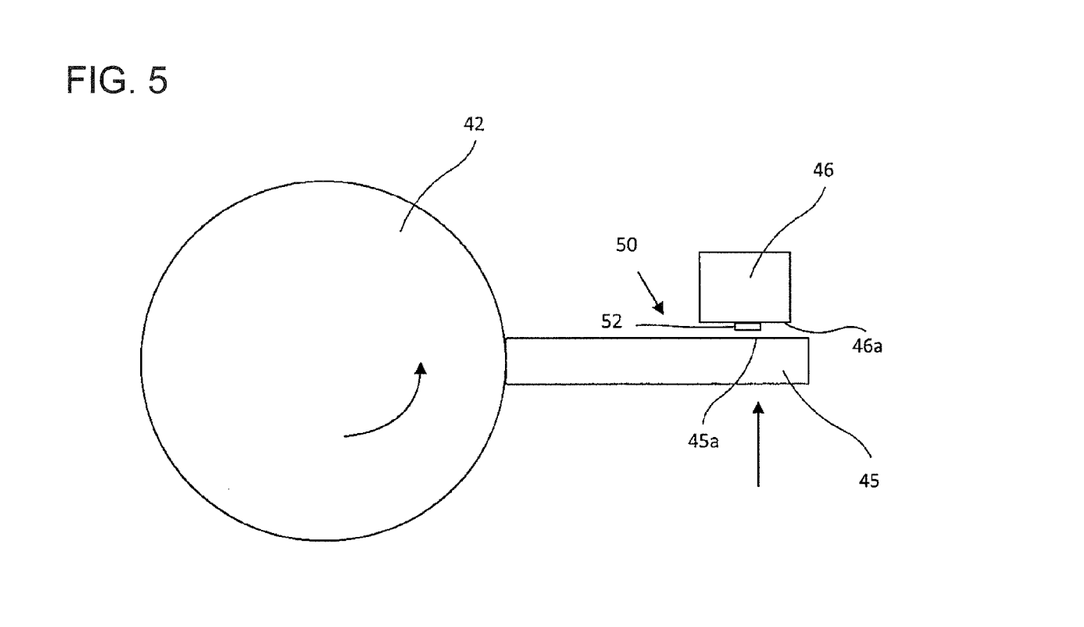
FIG. 5 is a diagram schematically illustrating a mode of a friction detecting unit.

Next, details of the friction detecting unit 50 are described. FIG. 5 is a diagram schematically illustrating a mode of the friction detecting unit.

As illustrated in FIG. 3 to FIG. 5, the friction detecting unit 50 includes a force detecting unit 52 which detects contact force between the first rotation stopping member 45 and the second rotation stopping member 46. In the example of FIG. 5, the force detecting unit 52 is at least one of a load cell, a strain gauge, a pressure sensor and a piezoelectric element, which is provided on a contact surface 46a of the second rotation stopping member 46 with the first rotation stopping member 45. Namely, torque is obtained on the basis of the distance from the rotation center of the rotating body 41 rotationally driven by the first electric motor 14 or the second electric motor 22 to the force detecting unit 52, and the contact force detected by the force detecting unit 52. Since the distance from the rotation center of the rotating body 41 to the force detecting unit 52 is constant, the sliding friction in the seal portion 44 is correlated with the contact force between the first rotation stopping member 45 and the second rotation stopping member 46. For example, as the sliding friction in the seal portion 44 increases, the contact force between the first rotation stopping member 45 and the second rotation stopping member 46 (contact force detected by the force detecting unit 52) increases. As the sliding friction in the seal portion 44 decreases, the contact force between the first rotation stopping member 45 and the second rotation stopping member 46 (contact force detected by the force detecting unit 52) decreases.

Any of the load cell, the strain gauge, the pressure sensor and the piezoelectric element detects the force arising due to the contact of the first rotation stopping member 45 with the second rotation stopping member 46. Notably, the force detecting unit 52 may be provided on the contact surface 45a of the first rotation stopping member 45 with the second rotation stopping member 46. Moreover, the force detecting unit 52 only has to be provided on at least one of the contact surface 45a and the contact surface 46a.

Figure 6:
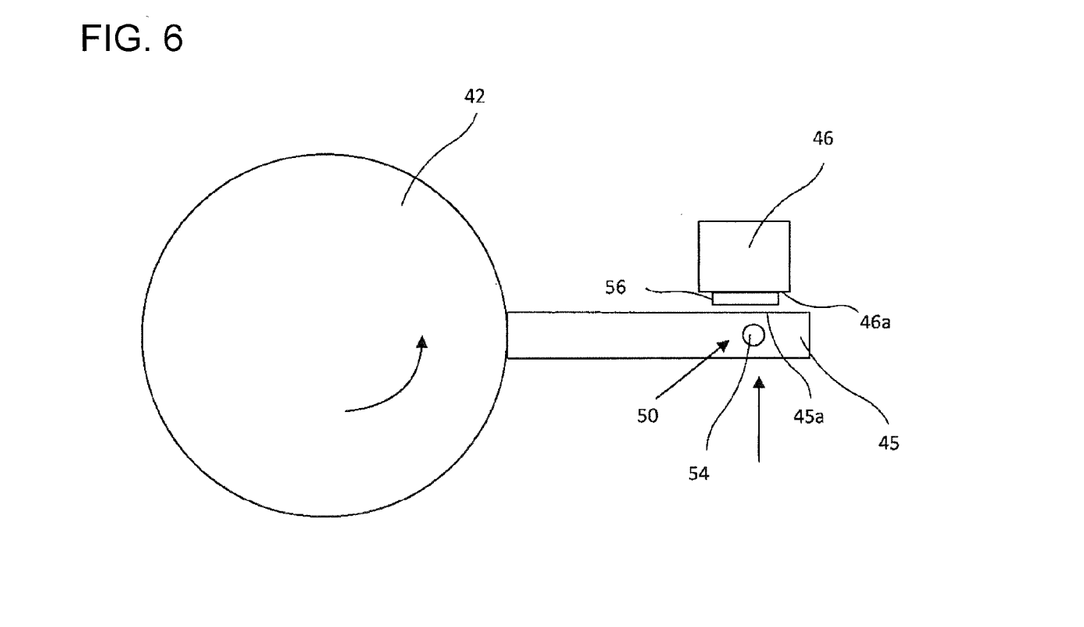
FIG. 6 is a diagram schematically illustrating a mode of a friction detecting unit.

Moreover, FIG. 6 is a diagram schematically illustrating a mode of the friction detecting unit. As illustrating in FIG. 6, the friction detecting unit 50 includes a motion detecting unit 54 which detects a physical quantity arising from the displacement of the first rotation stopping member 45. In the example of FIG. 6, the motion detecting unit 54 is at least one of a displacement sensor, a speed sensor and an acceleration sensor, which is provided on the first rotation stopping member 45. Namely, the sliding friction in the seal portion 44 is correlated with the displacement, the speed and the acceleration of the first rotation stopping member 45. For example, as the sliding friction in the seal portion 44 increases, the displacement, the speed and the acceleration of the first rotation stopping member 45 toward the second rotation stopping member 46 (physical quantity detected by the motion detecting unit 54) increases. As the sliding friction in the seal portion 44 decreases, the displacement, the speed and the acceleration of the first rotation stopping member 45 toward the second rotation stopping member 46 (physical quantity detected by the motion detecting unit 54) decreases.

Moreover, in the example of FIG. 6, an elastic member 56 is provided on the contact surface 46a of the second rotation stopping member 46 with the first rotation stopping member 45. The elastic member 56 is formed, for example, of rubber or the like and is a member which undergoes elastic deformation in accordance with the contact of the first rotation stopping member 45 and the second rotation stopping member 46 therebetween. Notably, the elastic member 56 may be provided on the contact surface 45a of the first rotation stopping member 45 with the second rotation stopping member 46. Moreover, the elastic member 56 only has to be provided on at least one of the contact surface 45a and the contact surface 46a. The elastic member 56 is provided for causing a further displacement of the first rotation stopping member 45 to arise due to the pressing force in the case where the first rotation stopping member 45 further presses the second rotation stopping member 46 in the state where the first rotation stopping member 45 and the second rotation stopping member 46 are in contact with each other.

End Point Detecting Apparatus

Next, details of the end point detecting apparatus 60 are described. As illustrated in FIGS. 3 and 4, the end point detecting apparatus 60 includes a signal processing unit 62 and an end point detecting unit 64.

The signal processing unit 62 generates a signal for detection of the polishing end point of the semiconductor wafer 18 on the basis of the current detected by the second current sensor (current detecting unit) 31 and the sliding friction detected by the friction detecting unit 50.

For example, the signal processing unit 62 can stop the output of the signal for detection of the polishing end point when it is detected that a change larger than a threshold is contained in the sliding friction detected by the friction detecting unit 50. Namely, that a change larger than a threshold is contained in the sliding friction detected by the friction detecting unit 50 means that some cause results in a change in sliding friction of the seal portion 44. In such a case, there can be a concern that the change in sliding friction of the seal portion 44 is superimposed on a first signal which is correlated with the current detected by the second current sensor (current detecting unit) 31, which can lead to false detection of the polishing end point of the semiconductor wafer 18. Therefore, in such a case, the output of the signal for detection of the polishing end point can be stopped, and thereby, false detection can be suppressed.

Moreover, for example, the signal processing unit 62 can output, as the signal for detection of the polishing end point, a difference between the first signal which is correlated with the current detected by the second current sensor 31 and a second signal which is correlated with the sliding friction detected by the friction detecting unit 50. Namely, the first signal contains the driving load due to the polishing friction force in polishing the semiconductor wafer 18 and the driving load due to the sliding friction of the seal portion 44 in the first or second rotary joint 40, 40'. Therefore, the signal processing unit 62 can subtract the second signal from the first signal, and thereby, can exclude the influence of the driving load due to the sliding friction of the seal portion 44 in the first or second rotary joint 40, 40', which can prevent false detection of the polishing end point from arising.

Moreover, for example, the signal processing unit 62 may include a band elimination filter which removes a predetermined frequency component in the second signal which is correlated with the sliding friction detected by the friction detecting unit 50. In this case, the signal processing unit 62 can output the signal for detection of the polishing end point on the basis of the second signal from which the predetermined frequency component removed by the band elimination filter and the first signal which is correlated with the current detected by the second current sensor 31. Namely, when some cause results in a change in sliding friction of the seal portion 44, there can be a case where the second signal contains a frequency band inherent thereto. Therefore, in the case where the inherent frequency band is known in advance, the signal processing unit 62 can remove the signal due to the change in sliding friction with the band elimination filter which removes the frequency band, which can prevent false detection of the polishing end point from arising.

Moreover, for example, the signal processing unit 62 can include an abnormality detection function in which a signal indicating abnormality arising in the first or second rotary joint 40, 40' is outputted when it is detected that a change larger than a threshold is contained in the sliding friction detected by the friction detecting unit 50. Namely, that a change larger than a threshold is contained in the sliding friction detected by the friction detecting unit 50 means that some cause results in a change in sliding friction of the seal portion 44. In such a case, there can be a concern that abnormality arises in the first or second rotary joint 40, 40'. Hence, warning can be outputted via an output interface such as a display and a speaker.

The end point detecting unit 64 detects the polishing end point of the semiconductor wafer 18 on the basis of the signal for detection of the polishing end point which is generated by the signal processing unit 62. Specifically, the end point detecting unit 64 determines the end point of polishing of the semiconductor wafer 18 on the basis of a change in signal for detection of the polishing end point which is outputted from the signal processing unit 62.

Figure 7:
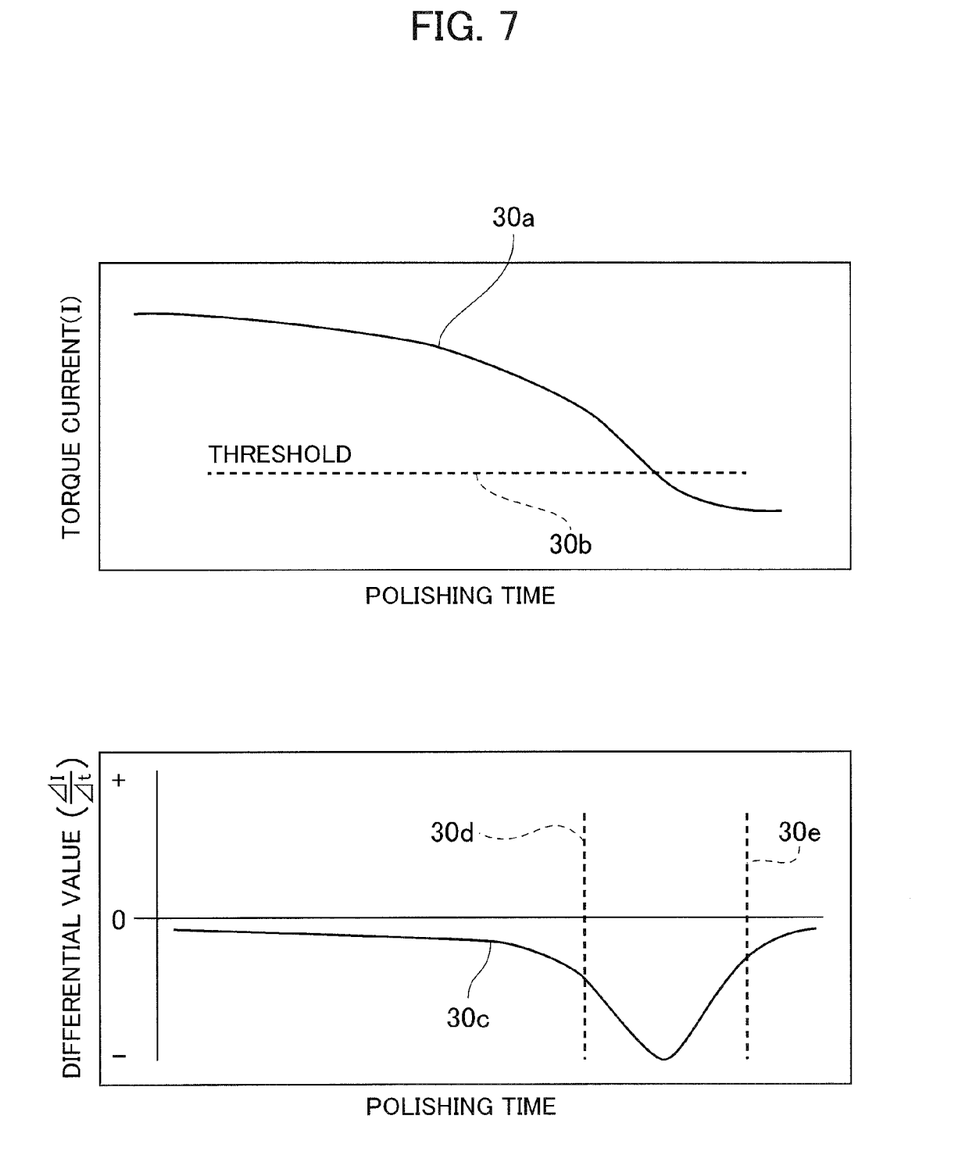
FIG. 7 is a diagram illustrating one example of a detection mode of an end point of polishing.

The determination of the polishing end point by the end point detecting unit 64 is described using FIG. 7. FIG. 7 is a diagram exemplarily illustrating a mode of the detection of the end point of polishing. In FIG. 7, the horizontal axis represents elapse of polishing time and the vertical axis represents a torque current (I) and a differential value ($\Delta I/\Delta t$) of the torque current.

For example, in the case where a torque current 30*a* (motor current of the V-phase) varies as in FIG. 7, the end point detecting unit 64 determines that polishing of the semiconductor wafer 18 reaches the end point when the torque current 30*a* becomes smaller than a preset threshold 30*b*.

Moreover, the end point detecting unit 64 can also obtain a differential value 30*c* of the torque current 30*a* to determine that polishing of the semiconductor wafer 18 reaches the end point when it is detected that the slope of the differential value 30*c* changes from being negative to being positive in a period between preset time thresholds 30*d* and 30*e*. Namely, the time thresholds 30*d* and 30*e* are set to give an approximate period during which polishing reaches the end point on the basis of empirical rules or the like, and the end point detecting unit 64 performs the end point detection on the polishing during the period between the time thresholds 30*d* and 30*e*. Due to this, except during the period between the time thresholds 30*d* and 30*e*, the end point detecting unit 64 does not determine that polishing of the semiconductor wafer 18 reaches the end point even when the slope of the differential value 30*c* changes from being negative to being positive. This is because, in the case where hunting of the differential value 30*c*, for example, due to unstable polishing in the occasion immediately after the start of polishing or the like results in a change of the slope from being negative to being positive, false detection of the polishing end point can be suppressed. Hereafter, a specific example of the determination of the polishing end point by the end point detecting unit 64 is described.

For example, it is considered that the semiconductor wafer 18 is obtained by layering different materials such as a semiconductor, a conductor and an insulator. In this case, the coefficient of friction is different between the layers of the different materials. Hence, when the polishing moves to a different material layer, the motor torque of the first electric motor 14 or the second electric motor 22 changes. In accordance with this change, the motor current (detection current signal) of the V-phase also changes. The end point detecting unit 64 detects that the motor current becomes larger or smaller than a threshold, and thereby, determines the end point of polishing of the semiconductor wafer 18. Moreover, the end point detecting unit 64 can also determine the end point of polishing of the semiconductor wafer 18 on the basis of a change in differential value of the motor current.

Moreover, for example, it is considered that the polishing flattens a polishing surface of the semiconductor wafer 18 which surface is not flat, to be a flat polishing surface. In this case, when the polishing surface of the semiconductor wafer 18 is made flat, the motor torque of the first electric motor 14 or the second electric motor 22 changes. In accordance with this change, the motor current (detection current signal) of the V-phase also changes. The end point detecting unit 64 detects that the motor current becomes smaller than a threshold, and thereby, determines the end point of polishing of the semiconductor wafer 18. Moreover, the end point detecting unit 64 can also determine the end point of polishing of the semiconductor wafer 18 on the basis of a change in differential value of the motor current.

As above, according to the first and second embodiments, accuracy of polishing end point detection can be improved. Namely, in the first and second embodiments, it is focused on that the current detected by the second current sensor 31 contains the driving load due to the sliding friction of the seal portion 44 in the first or second rotary joint 40, 40' as well as the driving load due to the polishing friction force in polishing the semiconductor wafer 18. In the present embodiments, the sliding friction of the seal portion 44 in the first or second rotary joint 40, 40' is detected, and the polishing end point of the polishing target is detected on the basis of the detected sliding friction and the current detected by the second current sensor 31. Hence, accuracy of polishing end point detection can be improved.

Moreover, according to the first and second embodiments, the presence or absence and the strength of a noise component contained in a signal outputted from the second current sensor 31 can be determined. By doing so, it can be determined whether or not the driving load due to the polishing friction force in polishing the semiconductor wafer 18 can be properly determined. Moreover, the signal processing in the signal processing unit 62 can remove the noise component contained in the signal outputted from the second current sensor 31 (the change in driving load due to the change in sliding friction of the seal portion 44 in the first or second rotary joint 40, 40'). Moreover, in a case such as where the signal outputted from the second current sensor 31 is not stable, for example, it can be determined whether or not the source of abnormality is in the first or second rotary joint 40, 40'. As described above, there can be provided a polishing apparatus compatible with needs for further higher resolution, prevention of false detection and detection of abnormality.

The previous description of embodiments is provided to enable a person skilled in the art to make and use the present invention. Moreover, various modifications to these embodiments will be readily apparent to those skilled in the art, and the generic principles and specific examples defined herein may be applied to other embodiments. Therefore, the present invention is not intended to be limited to the embodiments described herein but is to be accorded the widest scope as defined by limitation of the claims and equivalents.

REFERENCE SIGNS LIST

- 10 Polishing pad
- 12 Polishing table
- 14 First electric motor
- 18 Semiconductor wafer
- 20 Top ring
- 22 Second electric motor
- 31 Second current sensor (current detecting unit)
- 40 First rotary joint
- 40' Second rotary joint
- 41 Rotating body
- 42 Housing
- 43 Bearing
- 44 Seal portion
- 45a Contact surface
- 45 First rotation stopping member
- 46a Contact surface
- 46 Second rotation stopping member
- 50 Friction detecting unit
- 52 Force detecting unit
- 54 Motion detecting unit
- 56 Elastic member
- 60 End point detecting apparatus
- 62 Signal processing unit
- 64 End point detecting unit

What is claimed is:

1. A polishing apparatus comprising:
   a polishing table for holding a polishing pad for polishing a polishing target;
   a first driving unit that rotationally drives the polishing table;
   a first rotary joint that has a rotating body that is rotationally driven by the first driving unit, a housing provided around the rotating body, and a seal portion that seals between the rotating body and the housing;
   a current detecting unit that detects a current which is correlated with driving load of the first driving unit;
   a friction detecting unit that detects sliding friction in the seal portion of the first rotary joint; and
   an end point detecting apparatus that detects a polishing end point of the polishing target on the basis of the current detected by the current detecting unit and the sliding friction detected by the friction detecting unit.

2. The polishing apparatus according to claim 1, further comprising:
   a first rotation stopping member fixed to the housing; and
   a second rotation stopping member that comes into contact with the first rotation stopping member to stop rotation of the housing,
   wherein the friction detecting unit includes a force detecting unit that detects contact force between the first rotation stopping member and the second rotation stopping member.

3. The polishing apparatus according to claim 2, wherein the force detecting unit includes at least one of a load cell, a strain gauge, a pressure sensor and a piezoelectric element provided on at least one of contact portions between the first rotation stopping member and the second rotation stopping member.

4. The polishing apparatus according to claim 1, further comprising:
   a first rotation stopping member fixed to the housing; and
   a second rotation stopping member that comes into contact with the first rotation stopping member to stop rotation of the housing, wherein
   the friction detecting unit includes a motion detecting unit that detects a physical quantity caused by a displacement of the first rotation stopping member.

5. The polishing apparatus according to claim 4, wherein the motion detecting unit includes at least one of a displacement sensor, a speed sensor and an acceleration sensor provided on the first rotation stopping member.

6. The polishing apparatus according to claim 4, wherein on at least one of contact portions between the first rotation stopping member and the second rotation stopping member, an elastic member which undergoes elastic deformation in accordance with contact therebetween is provided.

7. The polishing apparatus according to claim 1, wherein the end point detecting apparatus includes
   a signal processing unit that generates a signal for detection of a polishing end point of the polishing target on the basis of the current detected by the current detecting unit and the sliding friction detected by the friction detecting unit, and
   an end point detecting unit that detects the polishing end point of the polishing target on the basis of the signal for detection of the polishing end point which is generated by the signal processing unit.

8. The polishing apparatus according to claim 7, wherein the signal processing unit stops output of the signal for detection of the polishing end point when it is detected that a change larger than a threshold is contained in the sliding friction detected by the friction detecting unit.

9. The polishing apparatus according to claim 7, wherein the signal processing unit configures a difference between a first signal which is correlated with the current detected by the current detecting unit and a second signal which is correlated with the sliding friction detected by the friction detecting unit, as the signal for detection of the polishing end point.

10. The polishing apparatus according to claim 7, wherein the signal processing unit includes a band elimination filter that removes a predetermined frequency component from a second signal which is correlated with the sliding friction detected by the friction detecting unit, and outputs the signal for detection of the polishing end point on the basis of the second signal from which the predetermined frequency component is removed by the band elimination filter and a first signal which is correlated with the current detected by the current detecting unit.

11. The polishing apparatus according to claim 7, wherein the signal processing unit includes an abnormality detection function in which a signal indicating that abnormality arises in the first or second rotary joint is outputted when it is detected that a change larger than a threshold is contained in the sliding friction detected by the friction detecting unit.

12. A polishing apparatus comprising:
   a substrate holding unit that holds a polishing target to be pressed onto a polishing pad for polishing the polishing target;
   a second driving unit that rotationally drives the holding unit;
   a second rotary joint that has a rotating body that is rotationally driven by the second driving unit, a housing provided around the rotating body, and a seal portion that seals between the rotating body and the housing;
   a current detecting unit that detects a current which is correlated with driving load of the second driving unit;
   a friction detecting unit that detects sliding friction in the seal portion of the second rotary joint; and
   an end point detecting apparatus that detects a polishing end point of the polishing target on the basis of the current detected by the current detecting unit and the sliding friction detected by the friction detecting unit.

13. The polishing apparatus according to claim 12, further comprising:
   a first rotation stopping member fixed to the housing; and
   a second rotation stopping member that comes into contact with the first rotation stopping member to stop rotation of the housing,
   wherein the friction detecting unit includes a force detecting unit that detects contact force between the first rotation stopping member and the second rotation stopping member.

14. The polishing apparatus according to claim 13, wherein the force detecting unit includes at least one of a load cell, a strain gauge, a pressure sensor and a piezoelectric element provided on at least one of contact portions between the first rotation stopping member and the second rotation stopping member.

15. The polishing apparatus according to claim 12, further comprising:
   a first rotation stopping member fixed to the housing; and
   a second rotation stopping member that comes into contact with the first rotation stopping member to stop rotation of the housing, wherein
   the friction detecting unit includes a motion detecting unit that detects a physical quantity caused by a displacement of the first rotation stopping member.

16. The polishing apparatus according to claim 15, wherein the motion detecting unit includes at least one of a displacement sensor, a speed sensor and an acceleration sensor provided on the first rotation stopping member.

17. The polishing apparatus according to claim 15, wherein on at least one of contact portions between the first rotation stopping member and the second rotation stopping member, an elastic member which undergoes elastic deformation in accordance with contact therebetween is provided.

18. The polishing apparatus according to claim 12, wherein the end point detecting apparatus includes
   a signal processing unit that generates a signal for detection of a polishing end point of the polishing target on the basis of the current detected by the current detecting unit and the sliding friction detected by the friction detecting unit, and
   an end point detecting unit that detects the polishing end point of the polishing target on the basis of the signal for detection of the polishing end point which is generated by the signal processing unit.

19. The polishing apparatus according to claim 18, wherein the signal processing unit stops output of the signal for detection of the polishing end point when it is detected that a change larger than a threshold is contained in the sliding friction detected by the friction detecting unit.

20. The polishing apparatus according to claim 18, wherein the signal processing unit configures a difference between a first signal which is correlated with the current detected by the current detecting unit and a second signal which is correlated with the sliding friction detected by the friction detecting unit, as the signal for detection of the polishing end point.

21. The polishing apparatus according to claim 18, wherein the signal processing unit includes a band elimination filter that removes a predetermined frequency component from a second signal which is correlated with the sliding friction detected by the friction detecting unit, and outputs the signal for detection of the polishing end point on the basis of the second signal from which the predetermined frequency component is removed by the band elimination filter and a first signal which is correlated with the current detected by the current detecting unit.

22. The polishing apparatus according to claim 18, wherein the signal processing unit includes an abnormality detection function in which a signal indicating that abnormality arises in the first or second rotary joint is outputted when it is detected that a change larger than a threshold is contained in the sliding friction detected by the friction detecting unit.

* * * * *